United States Patent [19]

Eggler et al.

[11] Patent Number: 5,298,512
[45] Date of Patent: Mar. 29, 1994

[54] SUBSTITUTED CHROMANS AND THEIR USE IN THE TREATMENT OF ASTHMA, ARTHRITIS AND RELATED DISEASES

[75] Inventors: James F. Eggler, Stonington; Anthony Marfat, Mystic; Hiroko Masamune, Noank; Lawrence S. Melvin, Jr., Ledyard, all of Conn.

[73] Assignee: Pfizer Inc., New York, N.Y.

[21] Appl. No.: 768,622

[22] PCT Filed: Apr. 7, 1989

[86] PCT No.: PCT/US89/01457
§ 371 Date: Sep. 30, 1991
§ 102(e) Date: Sep. 30, 1991

[51] Int. Cl.$^5$ .............. C07D 405/06; C07D 405/12; A61K 31/44; A61K 31/47
[52] U.S. Cl. ..................... 514/314; 546/176; 546/269; 514/311; 514/337
[58] Field of Search ............. 546/176, 269; 514/337, 514/314

[56] References Cited

U.S. PATENT DOCUMENTS

| | | | |
|---|---|---|---|
| 3,419,560 | 12/1968 | Bernstein et al. | 260/268 |
| 3,936,461 | 2/1976 | Schwender et al. | 260/289 R |
| 4,127,669 | 11/1978 | Connor et al. | 424/283 |
| 4,563,468 | 1/1986 | Batchelor et al. | 514/337 |
| 4,571,406 | 2/1986 | Evans et al. | 514/456 |
| 4,642,347 | 2/1987 | Kreft, III et al. | 514/456 |
| 4,661,596 | 4/1987 | Kreft, III et al. | 546/152 |

FOREIGN PATENT DOCUMENTS

| | | | |
|---|---|---|---|
| 0288077 | 10/1988 | European Pat. Off. | C07D 311/22 |
| 0292977 | 11/1988 | European Pat. Off. | C07D 311/22 |
| 0313295 | 4/1989 | European Pat. Off. | C07D 405/06 |

*Primary Examiner*—David B. Springer
*Attorney, Agent, or Firm*—Peter C. Richardson; Gregg C. Benson; A. Dean Olson

[57] ABSTRACT

Substituted chromans which by inhibiting 5-lipoxygenase enzyme are useful in the prevention or treatment of asthma, arthritis, psoriasis, ulcers, myocardial infarction, stroke and related disease states in mammals, pharmaceutical compositions thereof, a method of treatment therewith, and to intermediates useful in the synthesis thereof.

21 Claims, No Drawings

SUBSTITUTED CHROMANS AND THEIR USE IN THE TREATMENT OF ASTHMA, ARTHRITIS AND RELATED DISEASES

BACKGROUND OF THE INVENTION

The present invention is directed to substituted chromans of the formula (I), depicted below, which by inhibiting 5-lipoxygenase enzyme are useful in the prevention or treatment of asthma, arthritis, psoriasis, ulcers, myocardial infarction, stroke and related disease states in mammals. The present invention is also directed to pharmaceutical compositions, and to a method of treatment Kreft et al., in U.S. Pat. No. 4,661,596, describe compounds which are disubstituted naphthalenes, dihydronaphthalenes or tetralins having the formula

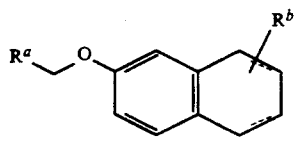

wherein the dotted lines represent optional double bonds, R is 2-pyridyl, 2-quinolyl, 2-pyrazinyl, 2-quinoxalinyl, 2-thiazolyl, 2-benzothiazolyl, 2-oxazolyl, 2-benzoxazolyl, 1-alkyl-2-imidazolyl or 1-alkyl-2-benzimidazolyl and R is hydroxy, lower alkoxy, lower alkyl or perfluoro alkyl. These compounds inhibit lipoxygenase enzyme and antagonize the effects of leukotriene D4, and so are useful in the prevention and treatment of asthma.

Eggler et al., in copending International application PCT/US87/02745 filed Oct. 19, 1987 have described similarly active compounds, including chromans of the formula

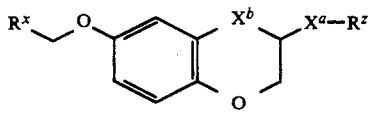

wherein $R^x$ is substantially defined as above, $R^z$ is aryl or heteroaryl, $X^a$ is, for example, oxygen or $CH_2$, and $X^b$ is C=O or CHOH. The present compounds generally fail to block leukotriene D4 receptors and so, in this respect, are differentiated from the compounds of Eggler et al., who also report certain structurally related compounds as intermediates (for example, compounds of the formula immediately above wherein $R^x$ is benzyl Many of these intermediates also find utility as intermediates in the present invention.

The chemical nomenclature employed herein generally follows that of "I.U.P.A.C Nomenclature of Organic Chemistry, 1979 Edition," Pergammon Press, New York, 1979.

SUMMARY OF THE INVENTION

The present invention is directed to compounds having the structural formula

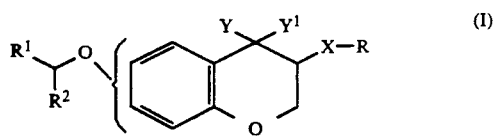

wherein

X is $CH_2$ or O;

Y and $Y^1$ are taken together and form a carbonyl group, or Y and $Y^1$ are taken separately, Y is hydrogen and $Y^1$ is hydroxy or an acyloxy group which is hydrolyzed to form a hydroxy group under physiological conditions;

R is attached by means of aromatic or heteroaromatic carbon and is phenyl, naphthyl, pyridyl, quinolyl, isoquinolyl, pyridazinyl, cinnolinyl, phthalazinyl, pyrimidinyl, naphthyridinyl, pyrrolyl, N-[($C_1$-$C_4$)alkyl]-pyrrolyl, indolyl, N-[($C_1$-$C_4$)alkyl]indolyl, isoindolyl, N-[($C_1$-$C_4$)alkyl]isoindolyl, indolizinyl, pyrazolyl, 1-[($C_1$-$C_4$)alkyl]pyrazolyl, indazolyl, 1-[($C_1$-$C_4$)alkyl]-1H-indazolyl, 2-[($C_1$-$C_4$)alkyl]-2H-indazolyl, imidazolyl, 1-[($C_1$-$C_4$)alkyl]imidazolyl, benzimidazolyl, 1-[($C_1$-$C_4$)alkyl]benzimidazolyl, furyl, benzofuranyl, isobenzofuranyl, oxazolyl, benzoxazolyl, isoxazolyl, benzo[c]isoxazolyl, benzo[d]isoxazolyl, thienyl, benzothiophenyl, isobenzothienyl, thiazolyl, benzothiazolyl, isothiazolyl, benzo[c]isothiazolyl, or benzo[d]isothiazolyl; or one of said groups which is mono- or disubstituted on carbon with the same or different groups which are bromo, chloro, fluoro, hydroxy, hydroxymethyl, ($C_1$-$C_4$)alkyl, ($C_1$-$C_4$)alkoxy, carboxy, [($C_1$-$C_4$)alkoxy]carbonyl, or substituted on adjacent carbons with trimethylene, tetramethylene, —CH$_2$—O—CH$_2$— or —O—CH$_2$—O—; or substituted on tertiary nitrogen to form an N-oxide; and either, in a first alternative, $R^1$ is phenyl, 2-, 3- or 4-pyridyl, 2-, 3-, 4 or 8-quinolyl, 1-, 3- or 4-isoquinolyl, 3- or 4-pyridazinyl, 3- or 4-cinnolinyl, 1-phthalazinyl, 2- or 4-pyrimidinyl, 2- or 4-quinazolinyl, 2-pyrazinyl, 2-quinoxalinyl, 1-, 2- or 3-indolizinyl, 2-, 4- or 5-oxazolyl, 2-benzoxazolyl, 3-, 4- or 5-isoxazolyl, 5-benzo[c]isoxazolyl, 3-benzo[d]isoxazolyl, 2-, 4- or 5-thiazolyl, 2-benzothiazolyl, 3-, 4- or 5-isothiazolyl, 5-benzo[c]isothiazolyl, 3-benzo[d]isothiazolyl, 1-[($C_1$-$C_4$)alkyl]-2-, 4- or 5-imidazolyl, 1-[($C_1$-$C_4$)alkyl]-2-benzimidazolyl, 1-[($C_1$-$C_4$)alkyl]-3-, 4- or 5-pyrazolyl, 2-[($C_1$-$C_4$)alkyl]-3(2H)-indazolyl, or 1-[($C_1$-$C_4$)alkyl]-3(1H)-indazolyl; or one of said groups mono- or disubstituted on carbon with the same or different substituents which are bromo, chloro, fluoro, ($C_1$-$C_4$)alkyl, trifluoromethyl, hydroxy, hydroxymethyl or ($C_1$-$C_4$)alkoxy, or on adjacent carbons with trimethylene, tetramethylene, —CH —O—CH$_2$— or —O—CH$_2$—O—; and $R^2$ is methyl, phenyl or phenyl mono- or disubstituted with the same or different substituents which are bromo, chloro, fluoro, ($C_1$-$C_4$)alkyl, trifluoromethyl, hydroxy, hydroxymethyl or ($C_1$-$C_4$)alkoxy, or on adjacent carbons with trimethylene, tetramethylene, —CH$_2$—O—CH$_2$— or —O—CH$_2$—O—; or, in a second alternative;

$R^1$ is 2-naphthyl or 2-naphthyl mono- or disubstituted with the same or different substituents which are bromo, chloro, fluoro, ($C_1$-$C_4$) alkyl, trifluoromethyl, hydroxy, hydroxymethyl or ($C_1$-$C_4$)alkoxy, or on adjacent carbons with trimethylene, tetramethylene, —CH$_2$—O—CH$_2$— or —O—CH$_2$—O—; and R$^2$ is hydrogen, methyl, phenyl or phenyl mono- or disubstituted with the same or different substituents which are bromo, chloro, fluoro, (C$_1$-C$_4$) alkyl, trifluoromethyl, hydroxy, hydroxymethyl or (C$_1$-C$_4$)alkoxy, or on adjacent carbons with trimethylene, tetramethylene, —CH$_2$—O—CH$_2$— or —O—CH$_2$—O—;

a pharmaceutically acceptable acid addition salt thereof when the compound contains a basic amine function; or a pharmaceutically acceptable cationic salt when . the compound contains a carboxy group.

Because of their ease of preparation and valuable biological activity, the preferred compounds of the formula (I) have R as either 3-pyridyl or 3-carboxyphenyl. When R$^1$ and R$^2$ are in the first alternative, the most preferred value of R$^1$ is unsubstituted naphthyl and the most preferred value of R$^2$ is hydrogen When R$^1$ and R$^2$ are in the second alternative, the preferred value of R$^1$ is 2-quinolyl and the preferred value of R$^2$ is methyl.

The bracket denotes attachment of the group R$^1$R$^2$CH—O— to either the C.6 or the C.7 position of the chroman ring. The more preferred point of attachment is generally C.6.

When Y and Y$^1$ are taken separately the structural formula (I) represent both cis- and trans-isomers, e.g., as follows

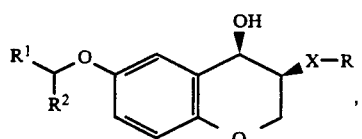

and

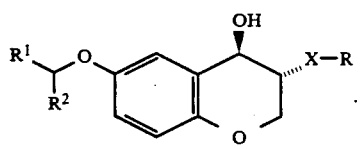

The cis-isomers (II) are generally preferred over corresponding trans-isomers (III) Fortunately, it is the preferred cis-isomer which usually predominates (sometimes with virtual exclusion of the trans-isomer) in the synthetic methods employed in preparation of the present compounds.

If desired, each of the isomers (II) and (III) can be resolved into a pair of optical isomers, for example, by formation of diastereomeric esters by coupling the alcohol with an optically active acid. Following conventional separation, e.g., fractional crystallization or chromatography, the individual diastereomeric esters are hydrolyzed to the pure, optically active enantiomers.

Said pharmaceutically-acceptable acid addition salts include, but are not limited to, those with HCl, HBr, HNO$_3$, H$_2$SO$_4$, H$_3$PO$_4$, CH$_3$SO$_3$H, p-CH$_3$C$_6$H$_4$SO$_3$H, CH$_3$CO$_2$H, gluconic acid, tartaric acid, maleic acid and succinic acid In the case of those compounds of the formula (I) which contain a further basic nitrogen, it will, of course, be possible to form diacid addition salts (e.g., the dihydrochloride) as well as the usual monoacid addition salt. Said pharmaceutically-acceptable cationic salts include, but are not limited to, those of sodium, potassium, calcium, magnesium, ammonia, N,N'-dibenzylethylenediamine, N-methylglucamine (meglumine), ethanolamine and diethanolamine.

The reference to Y$^1$ as an acyloxy group which is hydrolyzed to a hydroxy group under physiological conditions refers to esters of a type which are frequently referred to as "pro-drugs." Such esters are almost as well-known and common in the medicinal art as pharmaceutically-acceptable salts. Such esters are generally used to enhance oral absorption, but in any event are readily hydrolyzed in vivo to the parent . hydroxy compound. The more preferred acyloxy groups are those in which the acyl moiety is the alpha-aminoacyl residue of a naturally occurring L-alpha-amino acid,

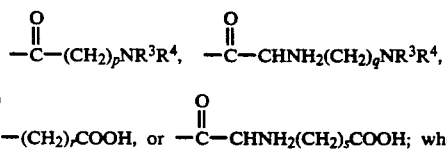

R$^3$ and R$^4$ are taken separately and are each independently hydrogen or (C$_1$-C$_4$)alkyl, or R$^3$ and R$^4$ are taken together with the nitrogen to which they are attached to form a pyrrolidine, piperidine, perhydroazepin or morpholine ring;

p is an integer from 1 to 4;
q is an integer from 1 to 3;
r is an integer from 2 to 3; and
s is an integer from 1 to 3.

Also forming a part of the present invention are pharmaceutical compositions for administration to a mammal which comprise a compound of the formula (I) and a pharmaceutically acceptable carrier; and a method of inhibiting 5-lipoxygenase enzyme in a mammal, particularly in man, so as to prevent or treat asthma, arthritis, psoriasis, gastrointestinal ulcers, stroke or myocardial infarction.

Of value in the present invention are intermediate compounds having the structural formula

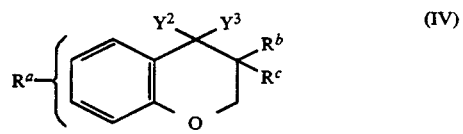

wherein
in the first alternative
Y$^2$ and Y$^3$ are taken together and form a carbonyl group, or Y$^2$ and Y$^3$ are taken separately, Y$^2$ is hydrogen and Y$^3$ is hydroxy; and R$g^a$ is hydroxy or benzyloxy;
R$^b$ and R$^c$ are taken separately, and R$^b$ is hydrogen and R$^c$ is -X-R; and
X and R are as defined above;
or in the second alternative
R$^b$ and R$^c$ are taken together and are hydroxymethylene or diazo; or R$^b$ and R$^c$ are taken separately,
R$^b$ is hydrogen and R$^c$ is bromo; and
R$^a$ is benzyloxy or

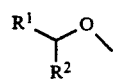

where $R^1$ and $R^2$ are as defined above.

DETAILED DESCRIPTION OF THE INVENTION

The present invention is readily carried out. Without regard to geometrical (cis-trans) or optical isomers, the compounds of the formula (I) wherein $Y+Y^1=$carbonyl, or $Y=H$ and $Y^1=OH$ are prepared according to the chemical transformations which are summarized in Flowsheets 1, 2 and 3, where the symbols R, $R^1$ and $R^2$ are as defined above. The various transformations found in these flowsheets, as well as transformations required for the preparation of the compounds (I) having other values of Y and $Y^1$, and methods for separation of cis-trans and optical isomers, are detailed below.

The condensation of Flowsheet 1 is typically carried out with the phenolic group in protected form as shown, methyl being a preferred protecting group only when X is $CH_2$. The preferred conditions employ a molar excess of the required aldehyde and a molar excess of a secondary amine such as pyrrolidine or piperidine as base. (It is understood that such a base facilitates the condensation by forming an enamine intermediate.) The reaction is generally carried out in a reaction-inert solvent, lower alcohols such as methanol being particularly well suited for this purpose. The temperature conditions for this transformation are not critical, e.g., 0°–70° C. is generally satisfactory, with ambient temperature particularly well suited as a matter of convenience.

As used here and elsewhere herein, the expression "reaction-inert solvent" refers to a solvent which does not interact with starting materials, reagents, intermediates or products in a manner which adversely affects the yield of the desired product.

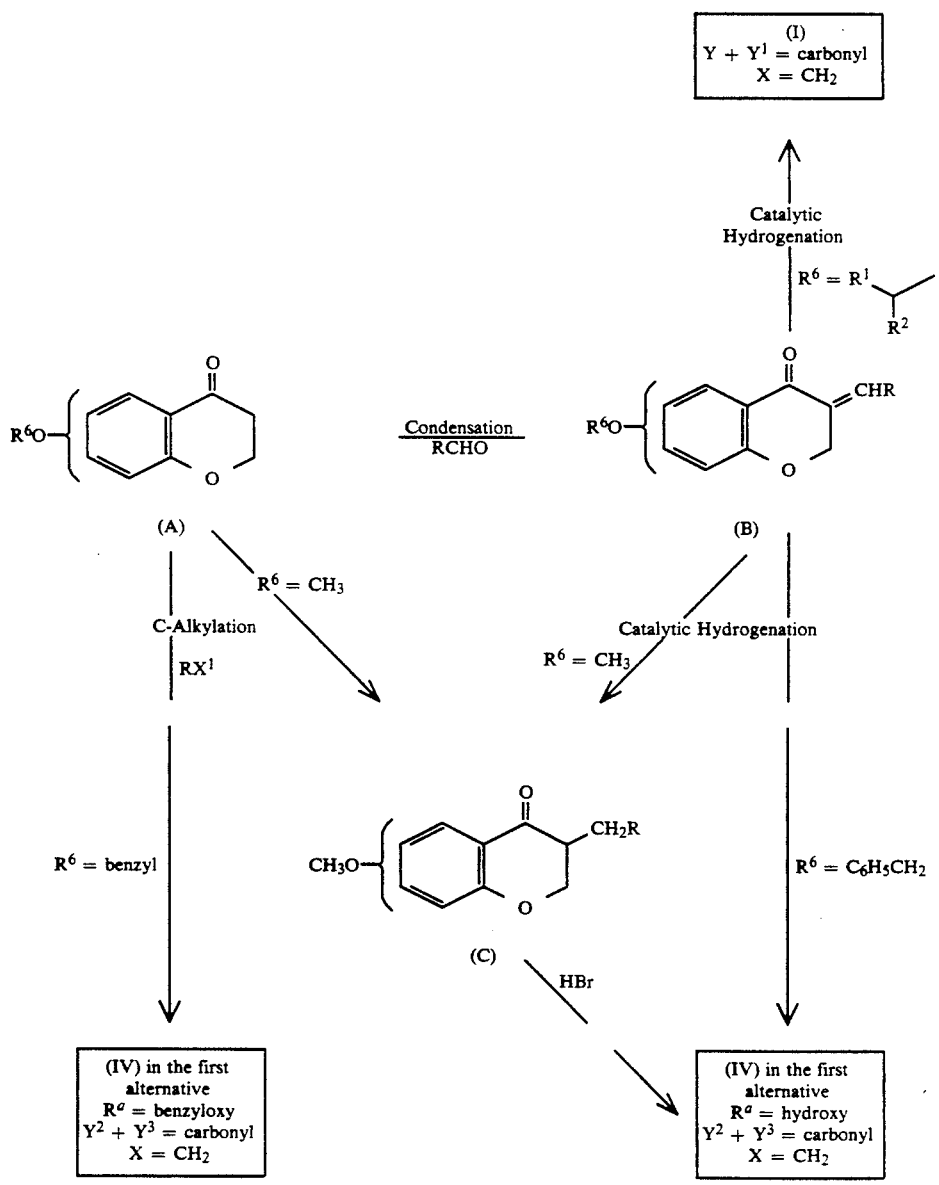

-continued

Flowsheet 1

When X = CH$_2$

R$^6$ = CH$_3$, C$_6$H$_5$CH$_2$ or R$^1$—CH(R$^2$)—

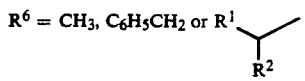

X$^1$ = Nucleophilically displaceable group such as I, Br, Cl, CH$_3$SO$_3$ or p-CH$_3$C$_6$H$_4$SO$_3$ Flowsheet 2

When X = O

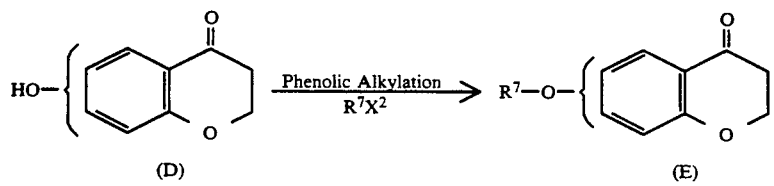

(D)  →  Phenolic Alkylation  R$^7$X$^2$  →  (E)

↙ Formylation        ↓ Bromination (IV) in the second alternative
Y$^2$ + Y$^3$ = carbonyl
R$^b$ + R$^c$ = hydroxymethylene
X = O (IV) in the second alternative
Y$^2$ + Y$^3$ = carbonyl
R$^b$ + R$^c$ = diazo
X = O

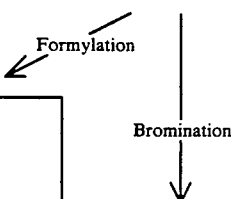
p-CH$_3$C$_6$H$_4$N$_3$
(a) R$^7$ = C$_6$H$_5$CH$_2$
(b) R$^7$ = R$^1$—CH(R$^2$)—

(IV) in the second alternative
Y$^2$ + Y$^3$ = carbonyl
R$^b$ = H, R$^c$ = Br
X = O (a) R$^7$ = R$^1$—CH(R$^2$)—

(b) R$^7$ = C$_6$H$_5$CH$_2$ (I)
Y + Y$^1$ = carbonyl
X = O (IV) in the first alternative
R$^a$ = benzyloxy
Y$^2$ + Y$^3$ = carbonyl
X = O R$^7$ = C$_6$H$_5$CH$_2$ or R$^1$—CH(R$^2$)—

X$^2$ = Cl, Br, I, CH$_3$SO$_3$, p-CH$_3$C$_8$H$_4$SO$_3$ or other nucleophilically displaceable group
(a) ROH, rhodium (II) acetate dimer
(b) ROH, base

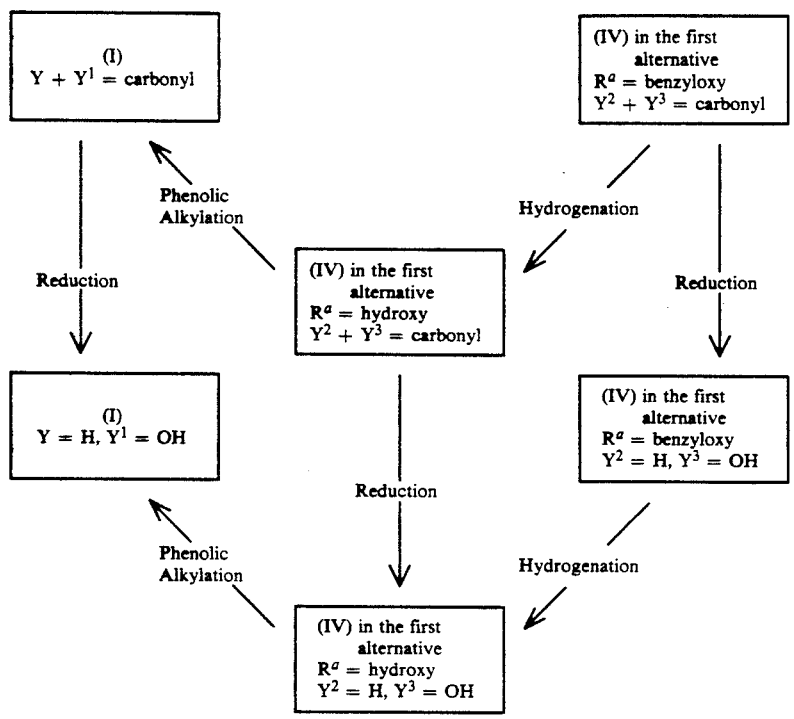

Flowsheet 3
When X = $CH_2$ or O

The C-alkylation of Flowsheet 1 is carried out by first converting the ketone (A) to its lithium salt, usually in situ, by the action of substantially one molar equivalent of a strong, sterically hindered base such as lithium diisopropylamide, usually carried out at low temperature (e.g., about $-40°$ to $-80°$ C. conveniently at the temperature of a dry ice-acetone bath). The salt in turn is reacted with the alkylating agent, preferably the highly reactive iodide, usually in molar excess in the presence of a molar excess of hexamethyl phosphoramide, now at higher temperature (e.g., about $0°$ to $40°$ C.). Conveniently, the latter reagents are added to the cold lithium salt solution, and the temperature allowed to rise to ambient temperature as the reaction proceeds. The salt preparation and alkylation reaction are usually carried out in the same reaction-inert solvent (e.g., tetrahydrofuran). It will be evident to those skilled in the art that any free hydroxy or carboxy groups in the alkylating reagent should be in protected form (vide supra).

The catalytic hydrogenation transformations (debenzylations, $H_2$-additions to double bond) of Flowsheets 1, 2 and 3 are carried out under conventional conditions, generally in a reaction-inert solvent, and preferably using a noble metal catalyst and moderate conditions of temperature (e.g., about $0°$ to $70°$ C.) and hydrogen pressure (e.g., about 1 to 10 atmospheres). While higher pressures may be desirable in selected instances, such moderate pressures permit the use of much less elaborate and expensive equipment. Suitable noble metal catalysts include platinum, palladium, rhenium, rhodium and ruthenium, either of the supported or non-supported type, as well as the known catalytic compounds thereof such as the oxides, chlorides, etc. Examples of suitable catalyst supports include carbon, silica and barium sulfate. The catalysts may be preformed or formed in situ by prereduction of an appropriate salt of the catalytic compound. Examples of preferred catalysts are 5% palladium-on-carbon, 5% platinum-on-carbon; 5% rhodium-on-carbon, platinum chloride, palladium chloride, platinum oxide and ruthenium oxide. Most preferred in the present instance is palladium-on-carbon. Solvents generally suitable for the present hydrogenation include lower alkanols, ethyl acetate and tetrahydrofuran.

The methyl ethers [compounds of the formula (C)] in Flowsheet 1 are deblocked to form the corresponding phenol derivative, again, by conventional methods; for example, using concentrated HBr, or $BBr_3$.

The phenolic alkylations found in Flowsheets 2 and 3 and the bromine replacement reaction of Flowsheet 2 each represent conventional nucleophilic displacement reactions. These displacements are generally carried out in the presence of a base of sufficient strength to convert the displacing phenol, alcohol or thiol to its salt, and in a quantity at least sufficient to neutralize the by-product acid ($HX^1$, HBr). In those substrates which contain an aliphatic alcohol group [e.g., a compound (IV) wherein $Y^2$ is H and $Y^3$ is OH], bases of sufficient strength to convert that group to the anion will generally be used in an amount no more than sufficient to convert the more acidic phenol to the salt. When either of the reactants contains a group of acidity similar to or greater than that of the nucleophilic displacing compound, such potentially interfering groups are best introduced in protected form (e.g., a heteroaromatic phenolic group as methoxy or benzyloxy, a carboxy group as methyl or benzyl ester, removable by hydrolysis or hydrogenolysis according to methods detailed elsewhere herein). The present nucleophilic displacements are carried out in a reaction-inert solvent, preferably one which is much less acidic than the displacing phenol, alcohol or mercaptan. Most preferred are polar, aprotic solvents such as dimethylformamide or acetone, usually with a molar excess of the more readily available of the two reactants. Temperature is not critical, e.g., about 10°–70° C. is usually satisfactory with ambient temperature most convenient. In one preferred variant, the phenol, alcohol or mercaptan is irreversibly converted to the anion with a base such as sodium hydride. Other preferred variants employ $K_2CO_3$ as base in the presence of NaI, or $Cs_2CO_3$ as base in the presence of CsI.

The formylation of Flowsheet 2 represents a conventional condensation type reaction of a ketone with an alkyl formate This reaction is generally in an aprotic reaction-inert solvent such as toluene in the presence of a strong base such as sodium hydride at moderate temperatures (e.g., 0°–70° C., conveniently at ambient temperature). The subsequent conversion to the diazo compound is conveniently accomplished with tosyl azide as the reagent, a reaction generally carried out at low temperature (e.g., about $-10°$ to $-60°$ C.) in the presence of molar excess of a tertiary amine (e.g., triethylamine) in a reaction-inert solvent such as $CH_2Cl_2$. In turn, the diazo compound is reacted with an appropriate alcohol or mercaptan in the presence of a catalytic amount of rhodium (II) diacetate dimer to form the desired ether or thioether. The latter transformation is generally carried out in an anhydrous reaction-inert solvent such as toluene at somewhat elevated temperature, e.g., about 50°–100° C. Substituent alcohol or carboxy groups which are not intended to react are preferably protected in this transformation, as in the case of the nucleophilic displacement reactions discussed above.

The "reduction" reactions of Flowsheet 3 require the reduction of a ketone to a secondary alcohol, for which a number of selective reagents are available. Where no other $LiAlH_4$ reducible groups (such as carboxy, methoxycarbonyl) are present, that reagent is well suited for this purpose. On the other hand, $NaBH_4$ is preferred as the reducing agent when such reducible groups are present. In either case, these hydride reductions are generally carried out in a reaction-inert solvent (such as tetrahydrofuran in the case of $LiAlH_4$, methanol or a combination of methanol and tetrahydrofuran in the case of $NaBH_4$). In either case, temperature is not critical, about 0° to 50° C. being generally satisfactory and ambient temperature preferred. The present reduction step offers the potential of producing a mixture of cis- and trans-isomers [as illustrated in the formulas (II) and (III)] and in the present hydride reduction, that is the result which is generally observed. If one or the other of these isomers is particularly desired, one can usually find a reduction method and set of conditions which will favor the desired isomer. For example, $NaBH_4$ reduction in the presence of cerium chloride will generally strongly favor the cis-isomer. Catalytic hydrogenation is also a generally useful reduction method, generally carried out under conditions which are somewhat more vigorous than those described above (e.g., more prolonged time, higher catalyst level, higher temperature and/or higher pressure). Pd/C catalyst tends to particularly favor formation of cis-isomer. However, by variation of the catalyst and conditions, it will be possible to modify or even reverse that tendency. Where both cis- and trans-isomers form in the present reduction, they are generally separable by standard chemical methods (e.g., selective or fractional crystallization, chromatography, and so forth).

Those ketone compounds of the formula (I) wherein Y and $Y^1$ form a carbonyl group, and of the formula (IV) in the first alternative, contain an asymmetric carbon at the alpha-position which is adjacent to the carbonyl group, and therefore are racemic compounds capable of resolution into optically active enantiomers, e.g., by conversion of the racemate into diastereomeric salts with an optically active acid, which are generally separable by a fractional crystallization process. Alternatively, if the substrate contains a carboxy group, separable diastereomeric salts are formed with an optically active organic amine. Optical activity can also be induced by use of an optically active reagent in the step by which the asymmetric carbon is formed, e.g., use of an optically active Wilkinson type catalyst, or a noble metal supported on an optically active support, in the hydrogenation step. The optically active ketones are also available by conventional reoxidation of an optically active alcohol of the next paragraph, e.g., via the Jones oxidation.

The hydroxy compounds of the formula (I) and (IV) wherein Y (or $Y^2$) is hydrogen and $Y^1$ (or $Y^3$) is OH contain two such asymmetric carbons—corresponding to two racemates and four optically active compounds. One of these racemates is the above noted cis-isomer, and the other the trans-isomer. Each of these racemates is capable of resolution into a pair of enantiomers via diastereomeric salts, as detailed in the preceding paragraph. It is preferred, however, to convert the racemic alcohol to corresponding diastereomeric esters or urethanes formed with an optically active acid or isocyanate. Such covalently bonded derivatives are generally subjectable to a broader variety of separation methods (e.g., chromatography) than are diastereomeric salts. Such diastereomeric esters are formed from the alcohol and the optically active acid by standard methods, generally those involving activation of the acid, e.g., as the acid chloride, as a mixed anhydride with an alkyl chloroformate, or with a dehydrative coupling agent such as dicyclohexylcarbodiimide. A preferred optically active acid in the present case is $N^{alpha}$-(t-butoxy)tryptophan. Once the resulting diastereomeric esters are separated, e.g., by chromatographic methods, they are hydrolyzed by conventional methods, e.g., aqueous acid or aqueous base, to obtain the enantiomeric, optically active alcohols.

The prodrug esters of the present invention are prepared by methods similar to those used in the synthesis of esters in the preceding paragraph. Esters with alpha-amino acids, including natural L-amino acids, will generally by prepared from the appropriate amino acid in which the alpha-amino group, substituent $NH_2$ or NH groups (e.g., lysine, ornithine, arginine, histidine, tryptophan), hydroxy groups (serine, homoserine, threonine, tyrosine), mercapto groups (cysteine) and substituent carboxy groups (glutamic acid, aspartic acid) are in protected form (e.g., N-benzyloxycarbonyl, O- and S-benzyl) generally removed by catalytic hydrogenation in a subsequent step. Similarly, in the case of esters with primary or secondary amino substituents, the acids will be coupled with amino groups protected. Such protection is, of course, unnecessary with those acids containing tertiary amino substituents. Finally, the carboxy substituted esters are most conveniently prepared from the cyclic anhydride:

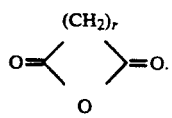

Concerning the biological activity of the present compounds, it is known that arachidonic acid is metabolized in mammals by means of two distinct pathways, one leading to prostaglandins and thromboxanes, the other to several oxidative products called leukotrienes, which are designated by letter number combinations such as B4, C4 and D4. The first step in this oxidative pathway is the oxidation of arachidonic acid under the influence of 5-lipoxygenase enzyme, an enzyme which is generally inhibited by the compounds (I) of the present invention, thus blocking the synthesis of all leukotrienes. That in itself provides the mechanism sufficient for the utility of the present compounds in the treatment or prevention of asthma (where LTC$_4$ and LTD4 are understood to be mediators), arthritis (where LTB4 is understood to be a mediator in inflammation), psoriasis (where LTB4 is understood to be a mediator), ulcers (where LTC$_4$ and LTD4 are understood to be mediators) and myocardial infarction (where LTB4 is understood to be a mediator). For a review concerning. leukotrienes, see Bailey et al., *Ann. Reports Med. Chem.* 17, pp. 203-217 (1982).

The in vitro activity of the compounds of the formula (I) is tested as follows RBL-1 cells, maintained in monolayer form are grown for 1 or 2 days in spinner culture in Minimum Essential Medium (Eagle) with Earl's Salts plus 15% Fetal Bovine Serum supplemented with antibiotic/antimycotic solution (GIBCO). The cells are washed 1 time with RPMI 1640 (GIBCO) and resuspended in RPMI 1640 plus 1 microM glutathione to a cell density of $1 \times 10^7$ cells/ml A volume of 0.5 ml of the cell suspension is incubated at 30° C. with 0.001 ml of dimethylsulfoxide solution of drug for 10 minutes. The reaction is started by a simultaneous addition of 0.005 ml (14C)-arachidonic acid in ethanol and 0.002 ml A23187 in dimethylsulfoxide to give final concentrations of 5.0 and 7.6 microM, respectively. After a 5 minute incubation at 30° C., the reaction is stopped by the addition of 0.27 ml acetonitrile/acetic acid (100/0.3) and the media is clarified by centrifugation. Analysis of the product profile is made by a 0.2 ml injection of the clarified supernatant into HPLC. The separation of radioactive products is effected on a radial PAX CN column (5 mm I.D., Waters) with a solvent system of acetonitrile/H$_2$O/acetic acid (0.1%) with a linear acetonitrile gradient from 35% to 70% over 15 minutes at 1 ml/minute. Quantitation is accomplished with a Berthold Radioactivity Monitor equipped with a built-in integrator and a 0.2 ml flow cell mixing 2.4 ml/minute Omnifluor (NEN) with column effluent Integration units for each product are calculated as a percentage of total integration units,. and then compared to the average control levels. The results are expressed as "Percent of Control" and are plotted vs the log of drug concentration. The IC$_{50}$ values are estimated by graphical inspection.

To evaluate the compounds of the formula (I) in vivo, they are tested by the so-called PAF lethality assay procedure:

Materials:

Mice: CD1 males, all approximately the same weight (approximately 26 grams), 12 per group.

Vehicle for oral drug dosing: EES (5% ethanol, 5% emulphor, 90% saline) Stored at room temperature.

Drugs: For routine screening at 50 mg/kg, 20 mg drug is dissolved in 4 ml EES, using sonication in a sonicator bath or grinding in a Ten Broeck grinder to dissolve drug if necessary. If solubility is still a problem, the drug is used as a suspension.

Vehicle for i.v. Injection: Saline with 2.5 mg/ml Bovine Serum Albumin (BSA, Sigma #A4378) 05 mg/ml Propranolol (Sigma #P0884) Prepared fresh daily and kept at room temperature.

Platelet Activating Factor (PAF): A 10 microM stock solution is prepared by dissolving 1 mg PAF (Calbiochem #429460) in 0.18 ml ethanol. This is stored at −20° C. and is diluted in vehicle (see above) the day of use. The concentration of PAF used is calibrated so that when injected at 0.1 ml/10 grams body weight, it will kill approximately 80% of untreated controls. This is usually about 0.028 g/kg (a 1 to 2034 dilution from stock). The solution is prepared in glass containers and is used with glass syringes to minimize surface adhesion by the PAF. It is kept at room temperature.

Positive Control: Phenidone is used at 25 mg/kg (its approximate ED 50).

Method:

45 minutes before PAF injection, mice are treated orally with drug using 0.1 ml/10 grams body weight. 35 to 40 minutes later they are placed under a heat lamp to dilate the caudal vein for PAF injection. PAF is injected i.v. at 0.1 ml/10 grams body weight, and death follows usually within 30 minutes, rarely after 60 minutes. Results are expressed as percent mortality as compared to controls. Because the assay appears to be sensitive to endogenous catecholamines (i.e., beta agonists protect the mice), Propranolol is used to overcome this potential problem. It also helps if the mice are acclimated to the room before testing, and if room noise and temperature are kept moderate and constant. The heat lamp distance should be calibrated so as to permit vasodilation without visible stress to the mice. Fasting the mice should be avoided Variations:

1. The time for oral dosing can be changed
2. Intravenous drug dosing is possible by coinjecting the drug with PAF in the same volume and vehicle as described above. For coinjection, PAF is prepared at twice the desired concentration in saline with BSA and Propranolol as above, and the drug is prepared at twice the desired concentration in the same vehicle. The two preparations are mixed in equal volumes immediately before injection.

Compounds of the present invention are tested for utility against stroke in gerbils according to the method of Gaudet et al., Stroke, vol. 11, pp. 648-652 (1980).

For use in the prevention or treatment of asthma, arthritis, psoriasis and gastrointestinal ulcers in a mammal, including man, a compound of the formula (I) is given in a 5-lipoxygenase inhibiting amount of about 0.5-50 mg/kg/day, in single or divided daily doses. A more preferred dosage range is 2-20 mg/kg/day, although in particular cases, at the discretion of the attending physician, doses outside the broader range may be required. The preferred route of administration is generally oral, but parenteral administration (e.g., intramuscular, intravenous, intradermal) will be preferred in special cases, e.g., where oral absorption is impaired as by disease, or the patient is unable to swallow.

The compounds of the present invention are generally administered in the form of pharmaceutical compositions comprising at least one of the compounds of the formula (I), together with a pharmaceutically acceptable vehicle or diluent. Such compositions are generally formulated in a conventional manner utilizing solid or liquid vehicles or diluents as appropriate to the mode of desired administration: for oral administration, in the form of tablets, hard or soft gelatin capsules, suspensions, granules, powders and the like; and, for parenteral administration, in the form of injectable solutions or suspensions, and the like.

The present invention is illustrated by the following examples, but is not limited to the details thereof.

EXAMPLE 1

6-Benzyloxy-3-(3-pyridyloxy)-4-chromanone

To a solution of 3-hydroxypyridine (8.56 g, 0.090 mol) in 300 ml of dimethylformamide was added NaH (60% in oil, 3.6 g, 0.090 mol). After stirring 0.5 hour, 6-benzyloxy-3-bromo-4-chromanone (30.0 g., 0.090 mol) was added in one portion. After stirring for 1 hour, the reaction mixture was poured into 1 liter of water and extracted 3×250 ml of ethyl acetate. The organic layers were combined, washed 1×100 ml $H_2O$, 1×100 ml 10% LiCl and 1×100 ml brine, dried ($Na_2SO_4$) and stripped to yield 40 g of crude title product, which was chromatographed on silica gel using 1:4 ethyl acetate:$CH_2Cl_2$ as eluant to yield 1.13 g of purified title product as an off-white powder; mp 133°–134° C. A portion (290 mg) was recrystallized from isopropyl ether to yield 240 mg of white powder.

EXAMPLE 2 cis-6-Benzyloxy-3-(3-pyridyloxy)-4-chromanol

Title product of the preceding Example (150 mg, 0.432 mmol) was dissolved in 2.5 ml of tetrahydrofuran and 4.0 ml of methanol and cooled to 0°–5° C. under $N_2$. $NaBH_4$ (18 mg, 0.475 mmol) was added in one portion and, after 40 minutes at 0°–5° C., the mixture warmed to ambient temperature, concentrated in vacuo, diluted with 70 ml ethyl acetate, washed twice with water and once with brine, dried ($Na_2SO_4$), stripped in vacuo and the residue recrystallized from hot isopropyl ether to yield 105 mg of present title product as an off-white powder; mp 124°–125° C.; $^1$H-NMR ($CDCl_3$) includes delta (ppm) 5.03 (s, 2H). HRMS 349.1174, calcd. 349.1315. Anal. C 71.77, H 5.42, N 3.88; calcd C 72.18, H 5.48, N 4.01.

EXAMPLE 3 cis-3-(3-Pyridyloxy)-4,6-chromandiol

Title product of the preceding Example (6.94 g, 19.9 mmol) in 80 ml of tetrahydrofuran and 160 ml of methanol was hydrogenated over 2.5 g of 10% Pd/C (50% water wet) at 50 psig for 20 hours Catalyst was recovered by filtration over diatomaceous earth. The filtrate was stripped in vacuo and the residue chromatographed on silica gel gradiently eluted with 1:20 to 1:10 $CH_3OH:CH_2Cl_2$ to yield 3.15 g of purified title product; m/e 259.1 (M+); $^1$H-NMR (DMSO-$d_6$) delta (ppm): 4.84 (m, 2H), 4.18 (m, 2H), 6.58–8.34 (7 aromatic H), 8.87 (br s, 1H), 5.52 (d, 1H).

EXAMPLE 4 cis-3-(3-Pyridyloxy)-6-(2-naphthyl)methoxy-4-chromanol

To title product of the preceding Example (500 mg, 1.93 mmol) and 2-(chloromethyl)naphthalene (341 mg, 1.93 mmol) in 10 ml anhydrous dimethylformamide was added 98 mg (2.03 mmol) of 50% NaH in oil. After stirring 17 hours, the mixture was poured into 200 ml $H_2O$ and extracted 3× with ethyl acetate. The organic layers were combined, washed twice with $H_2O$ and once with brine, dried ($Na_2SO_4$), and stripped in vacuo. The residue was chromatographed on silica gel, gradiently eluting with 1-2% $CH_3OH$ in $CH_2Cl_2$, to yield 582 mg of title product as white crystals. Recrystallization from isopropyl ether/$CH_2Cl_2$ gave 518 mg white plates; mp 156°–157° C.; HRMS 399.1466, calcd. 399.1417; $^1$H-NMR ($CDCl_3$) includes delta 5.20 ppm (s, 2H).

To prepare the hydrochloride salt, present title product (40 mg, 0.100 mmol) was dissolved in 10 ml of ethyl acetate and 5 ml of $CH_3OH$. 1N HCl in ether (0.150 ml, 0.150 mmol) was added and the mixture stirred 2 hours, then stripped to yield 43 mg of HCl salt as an off-white powder; mp 112°–114° C. (degassing at 75°–80° C.).

To prepare the dimethylaminoacetate ester of present title product, dimethylglycine hydrochloride (74.3 mg, 0.532 mmol), 4-dimethylaminopyridine (0.065 ml, 0.532 mmol) and dicyclohexylcarbodiimide (110 mg, . 0.532 mmol) were added sequentially to a solution of free base (170 mg, 0.426 mmol) in 20 ml of $CH_2Cl_2$. After 44 hours, dicyclohexylurea was recovered by filtration, the filtrate stripped in vacuo, and the oily residue chromatographed on silica gel using gradient elution with 1:19 to 1:9 $CH_3OH$:ethyl acetate to yield ester free base as a clear oil. The latter was dissolved in 6 ml ether and 2 ml ethyl acetate. 1N HCl in ether (0.945 ml) was added. After stirring for 1 hour, the mixture was stripped to yield the dimethylaminoacetate ester of title product as a dihydrochloride salt; HRMS 484.2016, calcd. for free base, 484.1999; Anal. C 58.37, H 5.74, N 4.79; calcd. C 58.68, H 5.77, N 4.72.

EXAMPLES 5–9

By the method of the preceding Example, the title product of Example 3 and the indicated reagent were converted to the following additional compounds, having properties as indicated:

5. 1-Phenylethyl bromide produces cis-6-(1-phenylethoxy)-3-(3-pyridyloxy)-4-chromanol; mp 115°–118° C.; HRMS 363.1422, calcd 363.1471; $^1$H-NMR (300 MHz, $CDCl_3$) includes delta 5.03 (s, 2H).

6. Benzyhydryl bromide produces cis-6-(diphenylmethoxy)-3-(3-pyridyloxy)-4-chromanol; mp 145°–146°; HRMS 425 1632, calcd. 425.1628. Anal. C 75.24, H 5.52, N 3.19, calcd C 75.15, H 5.53, N 3.25. Hydrodhloride salt; mp 152°–155° C.; $^1$H-NMR (300 MHz, $CDCl_3$) includes delta 5.11 (s, 1H) and 4.97 (s, 1H).

7. 1-(2-Naphthyl)ethyl bromide produces diasteromeric cis-6-[1-(2-naphthyl)ethoxy]-3-(3-pyridyloxy)-4-chromanols; mp 158°–159° C.; HRMS 413 1579,calcd. 413.1628; $^1$H-NMR (300 MHz, $CDCl_3$) includes delta 1.68 (d, 3H, J=6.4 Hz); and mp 122°–124° C.; HRMS 413.1770, calcd. 413.1628; $^1$H-NMR (300 MHz, $CDCl_3$) includes delta 1.68 (d, 3H, J=6.4 Hz).

8. (6-Fluoro-2-naphthyl)methyl bromide produces cis-6-[(6-fluoro-2-naphthyl)methoxy]-3-(3-pyridyloxy)-

4-chromanol; mp 141°–142° C.; HRMS 418.1483, calcd. 418.1454; Anal. C 71.67, H 4.67, N 3.21, calcd. C 71.93, H 4.83, N 3.36.

9. (6-Methoxy-2-naphthyl)methyl bromide produces cis-6-[(6-methoxy-2-naphthyl)methoxy]-3-(3-pyridyloxy)-4-chromanol; mp 168°–169° C.; HRMS 429.1533, calcd. 429.1577; Anal. C 72.03, H 5.25, N 3.19, calcd. C 72.70, H 5.40, N 3.26.

EXAMPLE 10 cis-(−)- and cis-(+)-N$^{alpha}$-(t-Butoxycarbonyl)-L-tryptophan Esters of 3-(3-Pyridyloxy)-6-(2-naphthyl)methoxy-4-chromanol Title product of Example 4 (2.32 g, 5.8 mmol) was combined with CH$_2$Cl$_2$ (35 ml) in a flame dried flask. N$^{alpha}$-(t-butoxycarbonyl)-L-tryptophan (1.95 g, 6.7 mmol) was added, followed by dimethylaminopyridine (0 818 g, 6.7 mmol) and finally dicyclohexylcarbodiimide (1.38 g, 6.7 mmol). The mixture was stirred for 18 hours, dicyclohexyl urea recovered by filtration, and the filtrate chromatographed directly on silica gel using 63:63:4 CHCl$_3$:hexane:2-propanol as eluant to separate the less polar and more polar diastereomeric title products. The less polar product, 1.98 g, was rechromatographed in the same system to yield 1.56 g of purified cis-(−)-title product, [alpha]$_D^{25}$=−38.46 (CHCl$_3$). Minor more polar product fractions from the second column were combined with more polar product fractions of the first column and stripped to yield 2.14 g of cis-(+)-title product; [alpha]$_D^{25}$=+37.12°(CHCl$_3$).

EXAMPLE 11 cis-(+)-6-(2-Naphthyl)methoxy-3-(3-pyridyloxy)-4-chromanol

The cis-(−)title ester of the preceding Example (1.75 g, 2.6 mmol) was combined with 35 ml of methanol and 20 ml of 1N NaOH and the mixture heated at reflux for 15 minutes, cooled, neutralized with 2N HCl, stripped of methanol, and the resulting white solids recovered by filtration and recrystallized from toluene to yield 639 mg of present title product; mp 180°–181° C.; HRMS 399.1436, calcd. 399.1471; [allpha]$_D^{25}$=+66.4° (CHCl$_3$); Anal. C 74.98, H 5.11, N 3.51, calcd C 75.17, H 5.30, N 3.51.

The corresponding hydrochloride salt was formed by dissolving 202 mg of this product in 10 ml tetrahydrofuran and adding 0.51 ml of 1N HCl in ether (1 equivalent), concentrating to dryness, three times adding toluene and restripping, and triturating the residue with ethyl acetate 185 mg; mp 85 ° C. (degassing), 190° (dec); HRMS 399.1436, calcd. 399.1471.

EXAMPLE 12 cis-(−)-6-(2-Naphthyl)methoxy-3-(3-pyridyloxy)-4-chromanol

By the method of the preceding Example, the cis-(+)-title product of Example 10 (2.14 g, 3 2 mmol) was converted to 848 mg of present title product; mp 180°–181° C.; [alpha]$_D^{25}$=−65.2°(CHCl$_3$); Anal. C 74.78, H 5.13, N 3.60, calcd. C 75.17, H 5.30, N 3.51.

A portion (203 mg) was converted to 186 mg of hydrochloride salt in like manner; mp 85° C. (degasses), 190° C. (dec).

EXAMPLE 13

6-Benzyloxy-3-(2-methyl-3-pyridyloxy)-4-chromanone

By the method of Example 1, 3-hydroxy-2-methylpyridine was converted to present title product; IR(CHCl$_3$) 1697, 1486 cm$^{-1}$; $^1$H-NMR (300 MH$_3$, CDCl$_3$) includes delta 2.48 (s, 3H) and 4.6 (m, 2H).

EXAMPLE 14 cis-6-Benzyloxy-3-(2-methyl-3-pyridyloxy)-4-chromanol

By the method of Example 2, the title product of the preceding Example was converted to present title product; mp 133°–134° C.; HRMS 363 1410 calcd 363.1471; Anal. C 72.23, H 5.72, N 3.81, calcd C 72.71, H 5.82, N 3.85.

By the method of Example 3, this compound is converted to 6-hydroxy-3-(2-methyl-3-(2-methyl-3-pyridyloxy)-4-chromanol, which in turn is converted to the corresponding 6-(substituted)oxy analogs of Examples 4–9 by the methods of those Examples.

EXAMPLE 15 cis-7-Benzyloxy-3-(3-pyridyloxy)-4-chromanol

By the method of Example 1, 7-benzyloxy-3-bromo-4-chromanone was converted to 7-benzyloxy-3-(3-pyridyloxy)-4-chromanone, which, by the method of Example 2 was converted to present title product, mp 73°–75° C.; HRMS 349.1302, calcd. 349 1315; $^1$H-NMR (300 MHz, CDCl$_3$) includes delta 5.04 (s, 2H).

EXAMPLE 16 cis-3-(3-Pyridyloxy)-7-(2-naphthyl)methoxy-4-chromanol

By the method of Example 3, the title product of the preceding Example was converted to cis-3-(3-pyridyloxy)-4,7-chromandiol, which, by the method of Example 4 was converted to present title product; mp 155°–158° C.; HRMS 399.1484, calcd. 399.1471; Anal. C 74.57, H 5.24, N 3.49, calcd. C 75.18, H 5.30, N 3.51.

By the further methods of Example 4, present title product was further converted to its N,N-dimethylglycine ester, dihydrochloride salt; mp 95° C. (dec); HRMS 484.2016, calcd. 484.1999; Anal. C 58.37, H 5.74, N 4.79, calcd. C 58.68, H 5.77, N 4.72.

EXAMPLE 17

6-Benzyloxy-3-(3-(methoxycarbonyl)benzylidene)-4-chromanone

A mixture of 17 g of 6-benzyloxy-4-chromanone, 11.3 g of 3-carbomethoxybenzaldehyde, 14.4 g of pyrrolidine, 100 ml of tetrahydrofuran and 300 ml of methanol was stirred at room temperature overnight. The volatiles were evaporated in vacuo to afford the crude product, which was purified by column chromatography on silica gel eluting with dichloromethane. The product fractions were combined and concentrated to an oil which crystallized upon trituration with methanol to give 17.2 g of title product, mp 109°–112° C.

EXAMPLE 18

6-Hydroxy-3-(3-methoxycarbonylbenzyl)-4-chromanone

A mixture of 17 g of the product of the preceding Example, 1.7 g of 10% Pd/C catalyst, 200 ml of tetrahydrofuran and 200 ml of methanol was hydrogenated in a Parr shaker at 40 psig for 3 hours. The catalyst was removed by filtration and the volatiles were evaporated in vacuo to give 10.6 g of title product. $^1$H-NMR(acetone-d$_6$)delta (ppm): 2.65-3.30 (m, 3H), 3.80 (s, 3H), 4.2 (dd, J=4 Hz, J=8 Hz, 2H), 6.80-8.30 (m, 7H).

EXAMPLE 19 cis- and trans-3-(3-Methoxycarbonylbenzyl)chroman-4,6-diol

By the methods of Example 39, the product of the preceding Example was converted to present chromatographed title products in about the same yields. This cis-isomer, mp 135°-137° C., is less polar and the trans-isomer, mp 158°-160° C., is more polar; tlc (7:3 CH$_2$Cl$_2$:ether) Rf 0.25 and 0.20, respectively.

EXAMPLE 20 cis-3-(3-Methoxycarbonylbenzyl)-6-(2-naphthyl)methoxy-4-chromanol

By the method of Example 4, using 3% ethyl acetate in CH$_2$Cl$_2$ as eluant in the chromatography, cis-title product of the preceding Example (296 mg, 0.942 mmol) was converted to 311 mg of present title product; HRMS. 454.2 (M+), 141.1 (base); $^1$H-NMR (300 MHz, CDCl$_3$) includes delta 3.91 (s, 3H), 5.13 (s, 2H).

EXAMPLE 21 cis-3-(3-Carboxybenzyl)-6-(2-naphthyl)methoxy-4-chromanol

To a solution of title product of the preceding Example (302 mg, 0.664 mmol) in 10 ml of methanol was added 5 ml of 1N NaOH. After 45 minutes of reflux, the methanol was removed in vacuo. The residue was diluted with water, the pH brought to 3 with 1N HCl, extracted 2× ethyl acetate, and the organic layer separated. The latter was washed 1× brine, dried (Na$_2$SO$_4$), concentrated to a volume of 10 ml, and allowed to crystallize at room temperature. Filtration gave 172 mg present title product, mp 183°-184° C.; $^1$H-NMR (300 MHz, DMSO-d$_6$) includes delta 5.18 (s, 2H); Anal. C 75.93, H 5.46, calcd. C 76.34, H 5.49.

EXAMPLE 22

6-Methoxy-3-(3-pyridyl)methylene-4-chromanone

To a 25° C. mixture of 20.0 g (0.112 mol) of 6-methoxy-4-chromanone and 18.09 g (0.169 mol) of 3-pyridinecarbaldehyde in 100 ml of methanol was added 14.1 ml (0.169 mol) of pyrrolidine. The resultant solution was allowed to stir 60 hours at 25° C., cooled to 0° C. and filtered to yield 17.07 g (57%) of the title compound, mp 127°-131° C.; MS (m/e) 267 (M+), 238, 161, 150 (100%), 135 and 107. IR (CHCl$_3$) 1671 (C=O), 1614, 1589 and 1566 cm$^{-1}$. $^1$H-NMR (CDCl$_3$) delta (ppm): 3.79 (s, OCH$_3$), 5.23 (d, J=1.5 Hz, CH$_2$), 6.86 (d, J=8 Hz, C-8 H), 7.06 (dd, J=8, 2 Hz, C-7 H), 7.37 (d, J=1.5 Hz, vinyl H), 7.36, 7.58, 7.75, 8.52 and 8.57 (multiplets, 5 ArH). Anal. C 71.72, H 4.85, N 5 16, calcd. C 71.90, H 4.90, N 5.24.

EXAMPLE 23

6-Methoxy-3-(3-pyridylmethyl)-4-chromanone

A mixture of 25.2 g (94.4 mmol) of the title product of the preceding Example and 2 g of 5% Pd/C/50% H$_2$O in 1 liter ethyl acetate was hydrogenated at 35 psig hydrogen for 18 hours. The reaction was filtered through diatomaceous earth with ethyl acetate wash, and the combined filtrate and wash evaporated to an oil. Trituration of this oil with diisopropyl ether gave the title compound as crystals, mp 82°-84° C. MS (m/e) 269 (M+), 252, 177, 150 (100%), 135, 118 and 107. IR (CHCl$_3$) 1685 (C=O), 1618 and 1578 cm$^{-1}$. $^1$H-NMR (CDCl$_3$) delta (ppm): 2.71 (dd, J=15, 10 Hz, 1 CH$_2$Ar), 2.86 (m, CH), 3.19 (dd, J=15, 6 Hz, 1 CH$_2$Ar), 3.75 (s, OCH$_3$), 4.07 (dd, J=11, 8 Hz, 1 CH O), 4.30 (dd, J=11, 6 Hz, 1 CH$_2$O), 6.82 (d, J=9 Hz, C-8 H), 7.03 (dd, J=9, 2 Hz, C-7 H), 7.10 (dd, J=7, 7 Hz, C-5 PyrH), 7.27 (d, J=2 Hz, C-5 H), 7.53 (d, J=7 Hz, C-4 PyrH) and 8.45 (m, 2 PyrH). Anal. C 71.31, H 5.58, N 5.15, calcd. C 71.13, H 5.57, N 5.12.

EXAMPLE 24

6-Hydroxy-3-(3-pyridylmethyl)-4-chromanone

A mixture of 13.75 g (51.1 mmol) of the title product of the preceding Example, 46 ml of concentrated hydrobromic acid and 47 ml of acetic acid was heated at reflux for 10 hours, and then stirred 12 hours at 25° C. The reaction was poured into 470 ml of ice and water and the pH adjusted to 7.5-8 with solid sodium bicarbonate. The precipitate formed was stirred 0.5 hours, filtered, washed with water and dried in vacuo to yield 11 79 g (90%) of the title compound, mp 163°-166° C.; MS (m/e) 255 (M+, 100%), 241, 163, 136, 120 and 108. IR(KBr) 1687 (C=O), 1625, 1598 and 1582 cm$^{-1}$. $^1$H-NMR (DMSO-d$_6$) delta (ppm): 2.69 (dd, J=11, 17 Hz, 1 CH$_2$Ar), 3.10 (m, CH and 1 CH$_2$Ar), 4.11 (dd, J=11, 11 Hz, 1 OCH$_2$), 4.27 (dd, J=11, 5 Hz, 1 OCH$_2$), 6.85 (d, J=8 Hz, C-8H), 6.98 (dd, J=8, 2 Hz, C-7H), 7.07 (d, J=2 Hz, C-5H), 7.31 (dd, J=9, 8 Hz, C-5 PyrH), 7.67 (d, J=8 Hz, C-4 PyrH), 8.42 (m, 2 PyrH) and 9.48 (s, OH); Anal. C 69.39, H 5.08, N 5.37, calcd. (¼ H$_2$O) C 69.35, H 5.24, N 5.39.

EXAMPLE 25 cis-3-(3-Pyridyl)methylchroman-4,6-diol

A mixture of the title product of the preceding Example (6.0 g, 0.023 mol) and cerium chloride heptahydrate (CeCl$_3$ 7H$_2$O; 5.25 g, 0 0141 mol) in methanol (125 ml) was cooled to 0°-5° C. and sodium borohydride (0.445 g, 0.0117 mol) was added in three portions. The reaction was stirred at room temperature for 0.5 hours. Methanol was then removed in vacuo and the foamy residue was treated with saturated NH$_4$Cl solution, followed by extraction with ethyl acetate. The organic layer was dried over MgSO$_4$ and concentrated in vacuo to a foam. The foam was treated with toluene and then pumped under high vacuum for several hours. This was repeated two more times to give present title product (5.7 g, 94%) MS (m/e) 257 (M+), 137, 120 and 101. $^1$H-NMR(DMSO-d$_6$) after D$_2$O exchange includes 4.22 (d, J=2 Hz, cis isomer CHOD) and 4.17 (d, J =4 Hz, trans isomer CHOD). This assay indicated about 4% contamination with the trans-isomer.

EXAMPLE 26 cis-6-(Diphenylmethoxy)-3-(3-pyridyloxy)-4-chromanol

To a solution of title product of the preceding Example (250 mg, 0.972 mmol) in 5 ml anhydrous dimethylformamide was added benzhydrol bromide (264 mg, 1.07 mmol). Sodium hydride (60% oil dispersion; 41 mg, 1.02 mmol was added in one portion, and the reaction stirred 16 hours, then diluted into 150 ml H$_2$O and extracted 3× with ethyl acetate. The organic layers were combined, washed 2× H$_2$O and 1× brine, dried (Na$_2$SO$_4$), stripped to 0.50 g brown oil, and flash chromatographed on 90 g of silica gel gradiently eluted with 2–5% CH$_3$OH in CH$_2$Cl$_2$ to yield 268 mg of title product, which was crystallized from isopropyl ether/CH$_2$Cl$_2$ to yield 103 mg of purified title product; mp 169°–170° C.; HRMS 423.1834, calcd. 423.1836; Anal. C 79.07, H 5.64, N 3.35, calcd. C 79.40, H 5.95, N 3.31.

EXAMPLE 27

3-(3-Pyridylmethyl)-6-[1-(2-quinolyl)ethoxy]-4-chromanone

A mixture of title product of Example 24 (1.00 g, 3.92 mmol), 1-(2-quinolyl)ethyl methanesulfonate (1.08 g, 4.30 mmol), acetone (4.1 ml) and finely ground, anhydrous K$_2$CO$_3$ (1.68 g, 12.2 mmol) was heated at 80° C. for 17 hours. The resulting solution was cooled, stripped of solvent and the residue taken into ml H$_2$O and 200 ml CH$_2$Cl$_2$. The aqueous layer was extracted 2× 200 ml fresh CH$_2$Cl$_2$, and the organic layers combined, dried (MgSO$_4$), stripped of solvent and flash chromatographed on silica gel using ethyl acetate as eluant to yield 521 mg of present title product as an oil; MS 410 (M+), 156 (base); HRMS 410.1643; IR (CHCl$_3$) 2966, 1686, 1484, 1284, 1074, 828 cm$^{-1}$.

EXAMPLE 28 cis- and trans-3-(3-Pyridylmethyl)-6-[1-(2-quinolyl)ethoxy]-4-chromanol

To a solution of title product of the preceding Example (456 mg, 1 11 mmol) in 5.6 ml of CH$_3$OH under N$_2$ at 0°–5° C. was added NaBH$_4$ (46 mg, 1.22 mmol) in one portion. The stirred mixture was slowly warmed to room temperature and stirred for 2 hours, then the solvent stripped in vacuo, the residue taken up in 50 ml of CH$_2$Cl$_2$ and 50 ml saturated NaCl, the layers separated and the aqueous layer extracted 2× 50 ml CH$_2$Cl$_2$. The combined organic layers were dried (MgSO$_4$), stripped to an oil and chromatographed on silica gel using 1:1:1:7 ethyl acetate:isopropanol:hexane:CH$_2$Cl$_2$ as eluant to yield 129 mg of the cis-isomer of present title product as a white solid and 41 mg of the trans-isomer as an oil. Cis-isomer; mp softens at 67° C.; MS 412 (M+), 156 (base); IR (CHCl$_3$) 2954, 1491, 1258, 1073, 778 cm$^{-1}$. Trans-isomer MS 412 (M+), 156 (base); $^1$H-NMR (300 MHz, DMSO-d$_6$) delta (ppm) 8.24–8.50 (m, 2H), 8.17 (d, J=8.9 Hz, 1H), 8.10 (d, J=8.7 Hz, 1H), 7 76 (d, J=8.9 Hz, 1H), 7.69 (t, J=6.9 Hz, 1H), 7.60 (d, J=8.8 Hz, 1H), 7.45–7.56 (m, 2H), 7.15–7.30 (m, 1H), 7 00 (d, J=2.4 Hz, 1H), 6.75 (dd, J=8.8, 2.4 Hz, 1H), 6.62 (dd, J=7.7, 4.8 Hz, 1H), 5.60 (q, J=6.6 Hz, 1H), 4.36 (d, J=5.6 Hz, 1H), 4.05 (dd, J=10.8, 4.2 Hz, 1H), 3.76 (dd, J=10.8, 6.6 Hz, 1H), 2.70 (dd, J=13.2, 8.4 Hz, 1H), 2.46 (dd, J=13.2, 9.0 Hz, 1H), 2.04–2.19 (m, 1H), 1 71 (d, J=6.6 Hz, 1H).

EXAMPLE 29 cis-3-(3-Pyridyloxy)-6-[1-(2-quinolyl)ethoxy]-4-chromanol

By the method of Example 4, the title product of Example 3 (270 mg, 1.04 mmol) and 1-(2-quinolyl)ethyl methanesulfonate (394 mg, 1.57 mmol) were converted to present title product, purified by chromatography on silica gel column using 3% CH$_3$OH in ether as eluant, to yield purified title product as an approximately 1:1 mixture of diastereoisomers; mp 75°–83° C.; MS 414 (M+), 156 (100%): Anal. C 69.68, H 5.42, N 6.38, calcd. C 69.43, H 5 59, N 6.48; IR (CHCl$_3$) 2956, 1575, 1490, 1256, 1073, 830 cm$^{-1}$.

EXAMPLE 30

6-Benzyloxy-3-(4-methoxyphenoxy)-4-chromanone

A solution of 76 g of 3-diazo-6-benzyloxy-4-chromanone and 76 g of p-methoxyphenol in 450 ml of toluene was heated to 110° C. in an oil bath. Rhodium (II) acetate dimer (225 mg) was added in one portion. After nitrogen evolution ceased (5 minutes), the reaction was allowed to cool to room temperature, diluted with ethyl acetate and washed with 10% sodium hydroxide to remove excess phenol. The organic layer was dried over sodium sulfate and evaporated in vacuo to give the crude product, which was purified by column chromatography on silica gel eluting with dichloromethane to give 5.5 g of present title product; mp 98°–100° C.; $^1$H-NMR (CDCl$_3$) delta (ppm) 3.85(s, 3H), 4.45–4.65 (m, 2H), 5.0–5.2 (m, 3H), 6.5–7.6 (m, 12H)

EXAMPLE 31 cis-3-(4-Methoxyphenoxy)-4,6-chromandiol

By the method of Example 3, the product of the preceding Example (5.5 g) was converted to present title product, 2 3 g, mp 187°–189° C.; HRMS 288.0989, calcd. 288.0998.

EXAMPLE 32 cis-3-(4-Methoxyphenoxy)-6-[1-(2-quinolyl)ethoxy]-4-chromanol

By the method of Example 29, using 1:2 ethyl acetate:hexane as chromatography eluant, product of the preceding Example (452 mg, 1.57 mmol) was converted to 507 mg of present title product; mp 58°–61° C.; MS 443 (M+, base); IR (CHCl$_3$) 3561, 2930, 1603, 1492, 1240, 1032, 829 cm$^{-1}$; Anal C 69.68, H 5.42, N 6.38, calcd. C 69.43, H 5.59, N 6.48.

By the further methods of Example 4, present title product was further converted to its N,N-dimethylglycine ester, dihydrochloride salt; mp 81°–85° C.; MS 528 (M+), 156 (base); IR (CHCl$_3$) 2950, 1646, 1492, 1166, 1019, 654 cm$^{-1}$.

EXAMPLE 33

7-Methoxy-3-(3-pyridyl)methylene-4-chromanone

By the method of Example 22, 7-methoxy-4-chromanone (10 g, 56 mmol) and 3-pyridinecarbaldehyde (7.8 g, 73 mmol) were converted to present title product, isolated directly from the reaction mixture by cooling to 0° C., 11.9 g; mp 176°–178° C.; MS 267 (M+, base peak). Anal. C. 71.94, H 4.93, N 5.05, calcd. C 71.90, H 4.90, N 5.24.

EXAMPLE 34

7-Methoxy-3-(3-pyridylmethyl)-4-chromanone

Title product of the preceding Example (12.85 g) in 300 ml CH$_3$OH was hydrogenated for 12 hours at 50 psig over 1.4 g of 10% Pd/C. Catalyst was recovered by filtration. The filtrate was stripped to an oil from which title product was crystallized by trituration with 200 ml of warm isopropyl ether, 9.89 g; mp 95°–99° C.;

MS 269 (M+), 122 (base); IR (CHCl$_3$) 2958, 1678, 1611, 1577, 1435, 1258, 837 cm$^{-1}$. Anal. C 70.94, H 5.54, N 5.06, calcd. C 71.13, H 5.57, N 5.12.

EXAMPLE 35

7-Hydroxy-3-(3-pyridylmethyl)-4-chromanone

By the method of Example 24, title product of the preceding Example (3.8 g) was converted to present title product, 3.37 g; mp 181°–190° C.; Anal. C. 69.96, H 5.16, N 5.33, calcd. for 0.25 H$_2$O C 69.35, H 5.24, N 5.39.

EXAMPLE 36

3-(3-Pyridylmethyl)-7-[1-(2-quinolyl)ethoxy]-4-chromanone

By the method of Example 29, using ether as chromatography eluant, title product of the preceding Example (740 mg, 2 90 mmol) was converted to 650 mg of present title product as a semi-solid; MS 410 (M+), 156 (base); IR (CHCl$_3$) 2967, 1678, 1607, 1437, 1246, 1213, 829 cm.$^{-1}$.

EXAMPLE 37 cis- and trans-3-(3-(Pyridylmethyl)-7-[1-(2-quinolyl)ethoxy]4-chromanol

By the method of Example 2, the title product of the preceding Example (1.095 g, 2.67 mmol) was reduced to a mixture of diasteromeric title products. Initial silica gel chromatography using 5% CH$_3$OH in ether gave two white solids: 510 mg of a mixture of two diasteromeric cis-isomers; mp 73° C. (softens), 84° C. (partial); MS 412 (M+), 156 (base); IR (CHCl$_3$) 3592, 2955, 1618, 1498, 1073, 658 cm$^{-1}$; and 350 mg of a mixture of two diasteromeric trans-isomers.

The trans-diastereomers were dissolved in 30 ml of ether and 1 ml of CH$_2$Cl$_2$, concentrated to 10 ml, allowed to stand for 18 hours and 135 mg of transdiastereomer A recovered by filtration; mp 147°–151° C.; MS 412 (M+), 156 (base); IR (CHCl$_3$) 3592, 2967, 1619, 1498, 1165, 1020, 660 cm$^{-1}$. The filtrate was stripped and the residue rechromatographed in like manner to yield 176 mg of trans-diastereomer B; mp 73° (partial), 173° C.; MS 412 (M+), 156 (base); IR (CHCl$_3$) 3595, 2961, 1619, 1498, 1164, 1133, 659 cm$^{-1}$.

EXAMPLE 38

7-(Diphenylmethoxy)-3-(3-pyridylmethyl)-4-chromanone

By the method of Example 4, using CH$_2$Cl and then 5% CH$_3$OH in ether as eluants on chromatography, benzhydryl bromide (1.16 g, 4.69 mmol) and title product of Example 35 (1.00 g, 3.92 mmol) were converted to 908 mg of methanol triturated title product as a white solid; mp 45° C. (partial), 100° C.; MS 421 (M+), 167 (base); IR (CHCl$_3$) 2959, 1677, 1608, 1575, 1436, 1200 cm$^{-1}$.

EXAMPLE 39 cis- and trans-7-(Diphenylmethoxy)-3-(3-pyridylmethyl)-4-chromanol

By the method of Example 2, using gradient elution with 0–5% CH$_3$OH in ether on chromatography, title product of the preceding Example (908 mg, 2.15 mmol) was converted to 441 mg of title cis-isomer, recrystallized from ether to yield 333 mg of further purified cis-isomer; mp 143°–146° C.; MS 423 (M+), 167 (base); IR (CHCl$_3$) 3590, 2953, 1617, 1495, 1162, 1114 cm$^{-1}$; and 251 mg of title trans-isomer, triturated with 1:1 ether:CH$_2$Cl$_2$ to yield 133 mg of further purified trans-isomer; mp 140°–150° C.; MS 423 (M+), 167 (base).

EXAMPLE 40

6-Benzyloxy-3-(3-(methoxycarbonyl)benzylidene)-4-chromanone

A mixture of 17 g of 6-benzyloxy-4-chromanone, 11.3 g of 3-carbomethoxybenzaldehyde, 14.4 g of pyrrolidine, 100 ml of tetrahydrofuran and 300 ml of methanol was stirred at room temperature overnight. The volatiles were evaporated in vacuo to afford the crude product, which was purified by column chromatography on silica gel eluting with dichloromethane. The product fractions were combined and concentrated to an oil which crystallized upon trituration with methanol to give 17.2 g of title product, mp 109°–112° C.

EXAMPLE 41

6-Hydroxy-3-(3-(methoxycarbonyl)benzyl)-4-chromanone

A mixture of 17 g of the product of the preceding Example, 1.7 g of 10% Pd/C catalyst, 200 ml of tetrahydrofuran and 200 ml of methanol was hydrogenated in a Parr shaker at 40 psig for 3 hours. The catalyst was removed by filtration and the volatiles were evaporated in vacuo to give 10.6 g of title product; $^1$H-NMR (acetone-d$_6$) delta (ppm): 2.65–3.30 (m, 3H), 3.80 (s, 3H), 4.2 (dd, J=4, J=8, 2H), 6.80–8.30 (m, 7H).

EXAMPLE 42 cis- and trans-3-(3-(Methoxycarbonyl)benzyl)chroman-4,6-diol

To a solution of 4.7 g of the title product of the preceding Example in 100 ml of methanol was added 550 mg of sodium borohydride. The reaction was stirred at room temperature for 1 hour, then quenched with water. The solvent was evaporated in vacuo and the residue dissolved in ethyl acetate and washed with water. The ethyl acetate layer was dried over sodium sulfate and evaporated in vacuo to afford the crude product mixture. It was separated by column chromatography on silica gel, eluting with dichloromethane/ether, yielding about 1 g each of the less polar cis-isomer, mp 135°–137° C.; and the more polar transisomer, mp 158°–160° C.; tlc (7:3 CH$_2$Cl$_2$:ether) Rf 0.25 and 0.20, respectively.

EXAMPLE 43 cis-3-(3-Carboxybenzyl)-6-[1-(2-quinolyl)ethoxy]-4-chromanol

With resulting concurrent hydrolysis of the methyl ester, and using 5% CH$_3$OH in ether as eluant on chromatography, the method of Example 29 was used to convert the title product of the preceding Example (467 mg, 1.49 mmol) to 196 mg of present title product; mp 70°–73° C. (partial); MS 455 (M+-1), 156 (base); IR (CHCl$_3$) 2923, 1672, 1490, 1262, 1195, 1076, 830 cm$^{-1}$.

PREPARATION 1

4-(2-Cyanoethoxy)anisole

4-Methoxyphenol (248 g), KOH (5.6 g) and acrylonitrile (397 ml) were dissolved in 1 liter of t-butanol and heated with stirring at 75° C. for 5 hours. The mixture was then cooled to room temperature and stripped in vacuo to solid residue, which was repulped in ether and insolubles recovered by filtration. The latter were taken up in 2 liters of ethyl acetate, washed in sequence with 1 liter each of H₂O, saturated NaHCO₃ and saturated NaCl, dried over MgSO₄ and restripped to yield purified title product, 199.4 g, mp 62°-64° C.

PREPARATION 2

6-Methoxy-4-chromanone

The title product of the preceding Example (199 g) was combined with 240 ml H₂O and 480 ml of concentrated HCl and heated at reflux overnight. The reaction mixture was cooled to room temperature and solids recovered by filtration. The latter were taken up in 2 liters of ethyl acetate, washed with 200 ml of H₂O, dried over MgSO₄ and stripped in vacuo to yield intermediate 3-(4-methoxyphenoxy)propionic acid, 195 g, mp 105°-107° C. The latter was added to 600 ml of hot, stirred polyphosphoric acid maintained at 75° C. and the mixture stirred for 2 hours. The temperature rose to a maximum of 89° C. over the first one-half hour, then fell to the 75° C. bath temperature. The reaction mixture was quenched into 3.2 liters of ice and water and extracted with 1.2 liters of ethyl acetate. The organic extract was extracted in sequence with 600 ml each of H₂O, saturated NaHCO and saturated NaCl, dried over MgSO₄ and stripped to 180 g of solids which were taken up in 400 ml CH₂Cl₂, treated with activated carbon and restripped to a like quantity of solids. The latter were recrystallized from isopropyl ether to yield purified title product, 120 g, mp 46°-48° C., identical with the commercial product.

PREPARATION 3

6-Hydroxy-4-chromanone

A solution of 36 g of the product of the preceding Preparation in 290 ml of acetic acid and 290 ml of 48%. hydrobromic acid was heated at reflux for 3 hours. The reaction was cooled and stripped in vacuo to crude product which was diluted with water (6 liters), cooled to 0°-5° C. and title product recovered by filtration, 25.7 g (80%), mp 133°-136° C. Optionally, the product is further purified by chromatography on silica gel using ethyl acetate/hexane as eluant.

By the same method, 7-methoxy-4-chromanone was converted to 7-hydroxy-4-chromanone.

PREPARATION 4

6-Benzyloxy-4-chromanone

A mixture of 25 g of the product of the preceding Preparation, 26.5 g of benzyl bromide and 28 g of potassium carbonate in 150 ml of acetone was heated at reflux overnight. The reaction was cooled and filtered to remove potassium carbonate. The filtrate was evaporated and the residue was dissolved in ethyl acetate and washed with water. The ethyl acetate layer was dried over sodium sulfate and evaporated in vacuo to obtain the crude product, which was purified by recrystallization from methylene chloride/hexane to give 29 g of title product, mp 107°-108° C. ¹H-NMR (acetone-d₆) delta (ppm): 2.7 (t, 2H), 4 4 (t, 2H), 5.08 (s, 2H), 7.2-7.5 (m, 3H)

By the same method, 7-hydroxy-4-chromanone was converted to 7-benzyloxy-4-chromanone.

PREPARATION 5

3-Hydroxymethylene-6-benzyloxy-4-chromanone

To a solution of 172.5 g of the product of the preceding Preparation in 1 7 liters of toluene containing 168 ml of ethyl formate and 3 5 ml of ethanol was added, in portions, 66 g of 50% sodium hydride. The reaction was allowed to stir at room temperature for 1 hour, then poured into 1 5 liters of ice and H₂O, and acidified to pH 4 with dilute hydrochloric acid. The aqueous layer was extracted with several portions of ethyl acetate. The organic layers were combined, dried over sodium sulfate and evaporated in vacuo to give the o crude product which was triturated with hexane to remove hydride oil. The resultant product crystallized on standing, mp 82°-85° C.

PREPARATION 6

3-Diazo-6-benzyloxy-4-chromanone

To a −10° C. solution of 35.3 g of title product of the preceding Preparation in 250 ml of dichloromethane containing 25.2 g of triethylamine was added dropwise a solution of 24.4 g of tosyl azide in 100 ml of dichloromethane. After complete addition, the reaction was allowed to warm to room temperature and stirred overnight. The reaction mixture was washed with water, dried over sodium sulfate and evaporated in vacuo to give the crude product, which was purified by column chromatography on silica gel eluting with dichloromethane to give 21 g of product, mp 100°-103° C. ¹H-NMR (CDCl₃) delta (ppm): 5.02 (d, J=4, 2H), 6.7-7.5 (m, 10H).

PREPARATION 7

6-Benzyloxy-3-bromo-4-chromanone

A slurry of title product of the preceding Preparation (50.0 g, 0.197 mol) in 2200 ml of ether was cooled to 0°-5° C. under N2. Bromine (10.1 ml, 0 197 mol) was added dropwise over 15-20 minutes and the mixture . further stirred for 30 minutes at 0°-5° C., then for 1 hour at ambient temperature. The mixture was washed 2× 500 ml H₂O and 1×400 ml brine, dried (Na₂SO₄) and stripped to yield 66.2 g of title product which was chromatographed on silica gel using gradient elution with 1:1 to 3:1 CH :hexane to yield 42.0 g of present title product as a tan powder. ¹H-NMR (CDCl₃) delta (ppm) includes 5.06 (s, 2H), 4.6 (m, 3H). m/e M+334/332.

By the same method 7-benzyloxy-4-chromanone was converted to 7-benzyloxy-3-bromo-4-chromanone.

We claim:

1. A compound of the formula (I)

wherein

X is CH₂ or O;

R is attached by means of heteroaromatic carbon and is pyridyl or pyridyl mono- or disubstituted on carbon with the same or different groups which are bromo, chloro, fluoro, hydroxy, hydroxymethyl, ($C_1$-$C_4$)alkyl, ($C_1$-$C_4$)alkoxy, carboxy, [($C_1$-$C_4$)alkoxy]carbonyl, or substituted or adjacent carbons with trimethylene, tetramethylene, —CH₂—O—CH₂— or —O—CH₂—O—; or substituted on tertiary nitrogen to form an N-oxide; and either R¹ is 2-, 3-, 4- or 8-quinolyl, or one of said groups mono- or disubstituted on carbon with the same or different substituents which are bromo, chloro, fluoro, $(C_1-C_4)$ alkyl, trifluoromethyl, hydroxy, hydroxymethyl or $(C_1-C_4)$alkoxy, or on adjacent carbons with trimethylene, tetramethylene, —CH₂—O—CH₂— or —O—CH₂—O—; and R² is methyl, phenyl or phenyl mono- or disubstituted with the same or different substituents which are bromo, chloro, fluoro, $(C_1-C_4)$alkyl, trifluoromethyl, hydroxy, hydroxymethyl or $(C_1-C_4)$alkoxy, or on adjacent carbons with trimethylene, tetramethylene, —CH₂—O—CH₂— or —O—CH₂—O—; or R¹ is 2-naphthyl or 2-naphthyl mono- or disubstituted with the same or different substituents which are bromo, chloro, fluoro, $(C_1-C_4)$alkyl, trifluoromethyl, hydroxy, hydroxymethyl or $(C_1-C_4)$alkoxy, or on adjacent carbons with trimethylene, tetramethylene, —CH₂—O—CH₂— or —O—CH₂—O—; and R² is hydrogen, methyl, phenyl or phenyl mono- or disubstituted with the same or different substituents which are bromo, chloro, fluoro, $(C_1-C_4)$alkyl, trifluoromethyl, hydroxy, hydroxymethyl or $(C_1-C_4)$alkoxy, or on adjacent carbons with trimethylene, tetramethylene, —CH₂—O—CH₂— or —O—CH₂—O—;

a pharmaceutically acceptable acid addition salt thereof when the compound contains a basic amine function; and a pharmaceutically acceptable cationic salt when the compound contains a carboxy group.

2. The compound of claim 1 wherein R is 3-pyridyl, X is CH₂, R¹ is 2-quinolyl and R² is methyl.

3. A compound of claim 1 having the formula

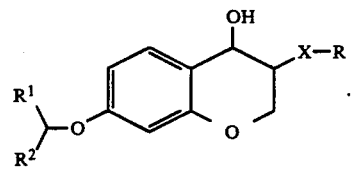

4. A compound of claim 7 wherein the —OH and —XR groups are cis.

5. The compound of claim 8 wherein R is 3-pyridyl, X is O, R¹ is 2-naphthyl and R² is hydrogen.

6. The compound of claim 4 wherein R is 3-pyridyl, X is CH₂, R¹ is 2-quinolyl and R² is methyl.

7. A compound of claim 1 having the formula

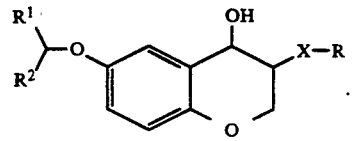

8. A compound of claim 7 wherein the —OH and —XR groups are cis.

9. A compound of claim 8 wherein R is 3-pyridyl.

10. The compound of claim 9 wherein X is CH₂.

11. The compound of claim 15 wherein R¹ is 2-quinolyl and R² is methyl.

12. A compound of claim 14 wherein X is O.

13. A compound of claim 17 wherein R¹ is 2-naphthyl or substituted 2-naphthyl and R² is hydrogen.

14. The compound of claim 18 wherein R¹ is 2-naphthyl, or an optically active isomer thereof.

15. The compound of claim 18 wherein R¹ is 7-fluoro-2-naphthyl.

16. The compound of claim 18 wherein R¹ is 7-methoxy-2-naphthyl.

17. The compound of claim 18 wherein R¹ is 2-naphthyl and R² is methyl.

18. A compound of claim 1 wherein R is 3-pyridyl, X is CH₂, R¹ is 2-quinolyl and R² is methyl.

19. A pharmaceutical composition for administration to a mammal which comprises a 5-lipoxygenase inhibiting amount of a compound of claim 1 and a pharmaceutically acceptable carrier.

20. A method of inhibiting 5-lipoxygenase in a mammal in need of such inhibition which comprises administering to said mammal a 5-lipoxygenase inhibiting amount of a compound of claim 1.

21. A method of claim 20 wherein the mammal is a human suffering from asthma, said compound administered to prevent or relieve the symptoms of said asthma.

* * * * *